United States Patent [19]
Swinehart

[11] Patent Number: 5,961,997
[45] Date of Patent: Oct. 5, 1999

[54] ANTIPRURITIC COMPOSITION

[76] Inventor: James M. Swinehart, 15 Sunset Dr., Englewood, Colo. 80110

[21] Appl. No.: 09/047,196

[22] Filed: Mar. 24, 1998

Related U.S. Application Data

[63] Continuation-in-part of application No. 08/823,975, Mar. 25, 1997, abandoned.

[51] Int. Cl.$^6$ ....................................................... A61K 7/48
[52] U.S. Cl. ............................................ 424/401; 514/846
[58] Field of Search ............................... 424/401; 514/846

[56] References Cited

U.S. PATENT DOCUMENTS

| | | | |
|---|---|---|---|
| 4,478,853 | 10/1994 | Chaussee et al. | 514/772 |
| 4,917,891 | 4/1990 | Kaufmann et al. | 424/401 |
| 5,322,689 | 6/1994 | Hughes et al. | 424/401 |
| 5,456,863 | 10/1995 | Bergmann | 252/547 |
| 5,516,793 | 5/1996 | Duffy | 514/474 |

FOREIGN PATENT DOCUMENTS

| | | |
|---|---|---|
| 281288 | 7/1988 | European Pat. Off. . |
| 281 288 | 9/1988 | European Pat. Off. . |
| 2401 489 | 7/1975 | Germany . |
| 54-1 45225 | 11/1979 | Japan . |
| 63-255219 | 10/1988 | Japan . |
| 07291856 | 11/1995 | Japan . |
| 07309756 | 11/1995 | Japan . |
| WO 91/12010 | 8/1991 | WIPO . |
| WO 93/17655 | 9/1993 | WIPO . |
| WO 93/24154 | 9/1993 | WIPO . |
| WO 95/03028 | 2/1995 | WIPO . |
| WO 97/20540 | 6/1997 | WIPO . |

OTHER PUBLICATIONS

Fulton, 1989, *J. Soc. Cosmet. Chem.*, 40:321–333.
Regine Cosmetics Catalog from Dermaline LLC, Apr. 1997.

*Primary Examiner*—Jyothsna Venkat

[57] ABSTRACT

Antipruritic compositions comprising menthol, camphor and phenol in a carrier. The compositions preferably further comprise lidocaine and pramoxine and more preferably further comprise lidocaine, pramoxine and hydrocortisone acetate. The compositions are oil-free, lanolin-free, fragrance-free, free of formaldehyde-releasing preservatives, hypoallergenic, noncomedogenic, and nonacnegenic. They relieve itching in patients suffering from a variety of dermatoses or pruritis. The carrier contains only ingredients rated 0 or 1 with respect to comedogenicity and irritancy.

7 Claims, No Drawings

ANTIPRURITIC COMPOSITION

This application is a continuation-in-part of application Ser. No. 08/823,975, filed Mar. 25, 1997 now abandoned.

FIELD OF THE INVENTION

The invention relates to antipruritic compositions comprising menthol, camphor and phenol in a carrier. The compositions may further comprise lidocaine and pramoxine. The compositions are hypoallergenic, noncomedogenic, nonacnegenic, oil-free, fragrance-free, lanolin-free, and free from formaldehyde-releasing preservatives. The carrier contains only ingredients rated 0 or 1 with respect to comedogenicity and irritancy.

BACKGROUND OF THE INVENTION

Cosmetics have been in use since Biblical times. They serve not only to soothe the skin and provide relief from minor irritations, but also to cover skin defects and to enhance beauty.

The physician's credo to "first, do no harm", however, is of considerable importance concerning skin care products. If aesthetic concerns were the only consideration with respect to cosmetics, another cosmetic line would certainly not be necessary.

However, potential problems exist with all cosmetics and skin care products currently on the market. Acne cosmetica is a problem seen all too frequently by the dermatologist. Comedogenicity is another major concern. Chemicals such as isopropyl myristate, steareth-16, isopropyl palmitate, cetyl alcohol, stearic acid, laureth-4, and many others, are major causes of acne among users. Oils or petroleum products, such as mineral oil, Jojoba oil or petrolatum, cause severe acne in many patients. Chemical peels, dermabrasion, dermal grafting, and/or laser surgery must be used to correct the resultant acne scarring. Yet, such chemicals and oils are still found in many cosmetic products currently on the market. Clearly, a need exists for a line of cosmetic and skin care products that would not initiate acne and, hence, would protect patients from the need for correction of disfiguring sequelae.

Many chemicals, though not comedogenic, frequently cause contact dermatitis. Indeed, many products on the market contain ingredients that are included in the North American Contact Dermatitis Society's standard patch test tray of 20 allergens. Products such as cetyl alcohol, stearyl alcohol, lanolin (which aggravates eczema or atopic dermatitis), propylene glycol, laureth-4, steareth-16, vitamin E, and other alcohols are frequent causes of contact dermatitis and irritant dermatitis. Imidazolidinyl urea and quaternium-15 are releasers of formaldehyde, the chemical responsible for some of the most severe cases of contact dermatitis seen by a dermatologist. Fragrances, including Balsam of Peru, cinammic alcohol and aldehyde, and numerous natural plant products and extracts, are the most common causes of contact dermatitis originating from cosmetics. Many patients also find perfumes offensive. No product can, of course, be "non-allergenic"; even water can cause a form of hives known as aquagenic urticaria. However, there is a need for a line of cosmetic and skin care products that avoids the use of disease-causing or disease-aggravating chemicals.

As a practicing dermatologist and dermatologic surgeon I feel that it is essential to design cosmetic and skin care products that contain effective concentrations of pertinent chemicals, while avoiding components known to be allergenic, irritating, acne-causing, or comedogenic. Such products should be aesthetically pleasing and yet avoid common clinical problems, such as acne, acne scarring, irritant dermatitis, photosensitivity, or allergic contact sensitization.

SUMMARY OF THE INVENTION

The present invention provides such skin care products. In particular, the invention provides antipruritic compositions comprising menthol, camphor and phenol in a carrier. The compositions preferably also contain lidocaine and pramoxine. The carrier contains only ingredients rated 0 or 1 with respect to comedogenicity and irritancy, preferably only ingredients rated 0 with respect to comedogenicity and irritancy. The antipruritic compositions of the invention are oil-free, fragrance-free, lanolin-free and free of formaldehyde-releasing preservatives. They are also hypoallergenic, noncomedogenic and nonacnegenic. Thus, the invention overcomes the disadvantages and problems associated with the use of prior art skin care products.

DEFINITIONS

A "noncomedogenic" composition is one that does not produce comedones (blackheads) or milia (small whiteheads).

A "nonacnegenic" composition is one that does not cause acne. A "papule" is a small erythematous acne bump. A "pustule" is a papule filled with pus. "Cysts" and "nodules" are larger acne lesions filled with pus. All three can be caused by comedogenic ingredients in cosmetic products.

"Hypoallergenic" compositions are those that contain only ingredients rated 0 or 1 with respect to irritancy, preferably only ingredients rated 0 with respect to irritancy, or which exhibit little or no allergenicity.

"Oil-free" compositions are those that do not contain animal or vegetable oils. Silicones do not fall into this category.

"Lanolin-free" compositions are those that do not contain lanolin, a wool alcohol, or its derivatives, including acetylated lanolin alcohol, anhydrous lanolin, lanolin alcohol, lanolin oil, or laneth-10.

"Fragrance-free" compositions are those that are free of both natural and artificial ingredients that possess a scent.

DETAILED DESCRIPTION OF THE PRESENTLY PREFERRED EMBODIMENTS OF THE INVENTION

The invention provides antipruritic compositions comprising combinations of antipruritic ingredients in a carrier. The carrier contains only ingredients rated 0 or 1 with respect to comedogenicity and irritancy. Preferably, the carrier contains only ingredients rated 0 with respect to comedogenicity and irritancy.

Many ingredients used in skin care products and shampoos have already been rated for comedogenicity and irritancy by James E. Fulton, Jr. These ratings have been published in Fulton, *J. Soc. Cosmet. Chem.*, 40, 321–333 (November/December 1989), the complete disclosure of which is incorporated herein by reference. A list of ingredients given ratings of 0 or 1 for comedogenicity and irritancy by Fulton that are suitable for use in the present invention is reproduced below in Table 1.

TABLE 1

INGREDIENTS WHOSE COMEDOGENICITY AND IRRITANCY ARE 0 OR 1

| Ingredient | Comedogenicity † | Irritancy ‡ |
|---|---|---|
| Fatty acids and their derivatives | | |
| Behenic acid | 0 | 0 |
| Behenyl erucate | 0 | 0 |
| Cetyl ester NF | 1 | 1 |
| Cetyl palmitate | 0 | 0 |
| Diisopropyl adipate | 0 | 0 |
| Diisopropyl dimerate | 0 | 0 |
| Octyldodecyl stearate | 0 | 0 |
| Octyldodecyl stearoyl stearate | 0 | 0 |
| Alcohols, sugars and their derivatives | | |
| SD alcohol 40 | 0 | 0 |
| Isopropyl alcohol | 0 | 0 |
| Butylene glycol | 1 | 0 |
| Hexylene glycol | 0–2* | 0–1 |
| PG dicaprylate/caprate | 1 | 0 |
| Ethylene glycol monostearate | 0 | 0 |
| Glucose glutamate | 0 | 0 |
| Sorbitol | 0 | 0 |
| Sorbitan sesquinoleate | 0–1* | 0 |
| Sorbitan stearate | 0 | 1 |
| PEG 40 sorbitan laurate | 0 | 0 |
| Polysorbate 20 | 0 | 0 |
| Polysorbate 80 | 0 | 0 |
| Glycerin | 0 | 0 |
| Glycereth-26 | 0 | 0 |
| Glyceryl stearate NSE | 1 | 0 |
| Glyceryl tricapylo/caprate | 1 | 1 |
| Behenyl triglyceride | 0 | 0 |
| Pentaerythrital tetra capra/caprylate | 0 | 0 |
| Polyethylene glycol (PEG 400) | 1 | 0 |
| Sucrose stearate | 0 | 0 |
| PEG 120 methyl glucose dioleate | 0 | 0 |
| PEG 20 stearate | 1 | 0 |
| PEG 100 stearate | 0 | 0 |
| Steareth-100 | 0 | 0 |
| Oleth-20 | 1 | 0 |
| Triacetin | 0 | 0 |
| PPG 30 cetyl ester | 0 | 0 |
| PPG 50 cetyl ester | 0 | 0 |
| PEG 78 glyceryl monococoate | 0 | 1 |
| PEG 8 castor oil | 1 | 1 |
| PEG 40 castor oil | 0 | 0 |
| Polypentaerythrital tetralaurate | 0 | 0 |
| Waxes | | |
| Candelilla wax | 1 | 0 |
| Carnuba wax | 1 | 0 |
| Ceresin wax | 0 | 0 |
| Emulsifying wax NF | 0 | 0–2* |
| Thickeners | | |
| Carboxymethylcellulose | 0 | 0 |
| Carboxypropylcellulose | 1 | 0 |
| Hydroxypropylcellulose | 1 | 0 |
| Magnesium aluminum silicate | 0 | 0 |
| Carbomer 940 | 1 | 0 |
| Bentonite | 0 | 0 |
| Kaolin | 0 | 0 |
| Talc | 1 | 0 |
| PVP | 0 | 0 |
| Pigments | | |
| D&C red #6 | 1 | 0 |
| D&C red #7 | 1 | 0 |
| D&C red #9 | 1 | 0 |
| Ultramarine violet | 0 | 0 |
| Iron oxides | 0 | 0 |
| Carmine | 0 | 0 |
| Titanium dioxide | 0 | 0 |
| Silicones | | |
| Simethicone | 1 | 0 |
| Dimethicone | 1 | 0 |
| Cyclomethicone | 0 | 0 |
| Sterols | | |
| Cholesterol | 0 | 0 |
| Soya sterol | 0 | 0 |
| Peg 5 soya sterol | 0 | 0 |
| Peg 10 soya sterol | 0 | 1 |
| Choleth 24 | 0 | 0 |
| Sterol esters | 0 | 0 |
| Vitamins and herbs | | |
| Tocopheryl acetate | 0 | 0 |
| Black walnut extract | 0 | 0 |
| Papain | 0 | 0 |
| Chamomile extract | 0 | 0 |
| Panthenol | 0 | 0 |
| Preservatives and additives | | |
| Methyl paraben | 0 | 0 |
| Propylparaben | 0 | 0 |
| Phenoxyethyl paraben | 0 | 0 |
| Allantoin | 0 | 0 |
| Hydantoin | | |
| Sodium hyaluronate | 0 | 0 |
| Chondroitin sulfate | 0 | 0 |
| Precipitated sulfur | 0 | 0 |
| Miscellaneous | | |
| Octyl dimethyl PABA | 0 | 0 |
| Oxybenzone | 0 | 0 |
| Octyl methoxycinnamate | 0 | 0 |
| Octyl salicylate | 0 | 0 |
| Acetone | 0 | 0 |
| Ethyl ether | 0 | 0 |
| Diethylene glycol monoethyl ether | 0 | 0 |
| Ethylene glycol monomethyl ether (EGME) | 0 | 0 |
| Lithium stearate | 1 | 0 |
| Magnesium stearate | 1 | 0 |
| Zinc oxide | 1 | 0 |
| Zinc stearate | 0 | 0 |
| Amoniomethylpropinate | 0 | 0 |
| Sodium PCA | 0 | 0 |
| Hydrolyzed animal protein | 0 | 0 |

† Comedogenicity or ability of test substance to produce follicular hyperkeratosis.
‡ Irritancy or ability of test substance to produce surface epithelial irritation.
*Results depend on source of raw material.

Other ingredients may be tested and rated for comedogenicity as described in Fulton, *J. Soc. Cosmet. Chem.*, 40, 321–333 (November/December 1989). Briefly, the ingredients to be tested are mixed in propylene glycol at a 9 to 1 dilution (10% concentration). New Zealand albino rabbits that have genetically good ears and are free from mites are used. Three rabbits, weighing two to three kilograms, are used for each assay. Animals are housed singly in suspended cages and fed Purina Rabbit Chow and water ad libitum. Animals are maintained on a 12-hour light and 12-hour dark cycle. A dose of 1 ml of the test material is applied and spread once daily to the entire inner surface of one ear, five days per week, for two weeks. The opposite untreated ear of each animal serves as an untreated control. Follicular keratosis is judged both macroscopically (visually) and microscopically with a micrometer to measure the width of the follicular keratosis. The macroscopic response is determined by averaging the measurements of the width of six follicles using a micrometer. A similar microscopic micrometer measurement is obtained by averaging the width of six follicles under a magnification of 430× after a 6-mm biopsy specimen is fixed in formalin, sectioned at six microns, and stained with hematoxylin-eosin. The results are then combined on a scale of one to five:

| Micrometer reading | Grade | |
|---|---|---|
| 0.009 in. or less | 0 | No significant increase in follicular keratosis |
| 0.010–.014 in. | 1 | |
| 0.015–.019 in. | 2 | A moderate increase in follicular keratosis |
| 0.020–.025 in. | 3 | |
| 0.025–.029 in. | 4 | An extensive increase in follicular keratosis |
| 0.030 in. or more | 5 | |

Grade 5 is the presence of large comedones throughout the ear, similar to those induced by the application of the standard "positive" testing agent, isopropyl myristate.

The irritancy produced by the repeated application of a chemical or skin care product on the surface epidermis in the rabbit ear is also evaluated on a similar scale of 0 to 5. The grades are summarized as follows:

| | |
|---|---|
| 0 | No irritation |
| 1 | Few scales, no erythema |
| 2 | Diffuse scaling, no erythema |
| 3 | Generalized scaling with erythema |
| 4 | Scaling, erythema, and edema |
| 5 | Epidermal necrosis and slough |

A quick review of the ingredient lists of all currently marketed skin care products always reveals one or more major offenders (i.e., those ingredients having ratings of 2 or greater) present on Fulton's list (see Table 2 below). Despite this, one frequently encounters claims of noncomedogenicity, nonirritancy and hypoallergenicity for cosmetic and skin care products currently on the shelf. It is quite possible that the test samples required for acnegenicity claims (25 patients) or allergenicity claims (50 to 200 patients) by manufacturers of these products may be too small to detect problems that dermatologists frequently see among larger or more varied patient populations, allowing these claims to be made for products that are not truly nonacnegenic or hypoallergenic. However, on a larger scale, it is important to avoid comedogenic, acnegenic, or irritating ingredients in any cosmetic invention.

TABLE 2

COMEDOGENICITY RATINGS AND IRRITANCY RATINGS FOR COMMONLY USED COSMETIC INGREDIENTS

| Component | Comedogenicity Rating | Irritancy Rating |
|---|---|---|
| Petrolatum | 5 | 0 |
| Cetyl Alcohol | 2 | 2 |
| Stearic Acid | 2–3 | 0 |
| Stearyl Alcohol | 2 | 2 |
| Lanolin Products | 0–4 | 0–3 |
| Triethanolamine | 2 | 0 |
| Fragrance | 0 | 0–5+ |
| Imadazolidinyl urea (formaldehyde releaser) | 0 | 0–5+ |
| Quaternium-15 (formaldehyde releaser) | 0 | 0–5+ |

TABLE 2-continued

COMEDOGENICITY RATINGS AND IRRITANCY RATINGS FOR COMMONLY USED COSMETIC INGREDIENTS

| Component | Comedogenicity Rating | Irritancy Rating |
|---|---|---|
| Propylene Glycol | 0 | 0–5+ |
| Laureth-4 | 4 | 4 |
| Steareth-16 | 5 | 1–3 |
| Isopropyl Myristate | 2–4 | 3 |
| Isopropyl Palmitate | 5 | 1 |
| Oils | 4 | 1–2 |
| Many dyes | 1–3 | 1–2 |
| Vitamin E | 0–3 | 0–3 |
| Comedogenic or Irritating Alcohols | 1–5 | 1–5 |

One important point for discussion and consideration is the concentration of such comedogenic/irritating chemicals in the actual marketed products. Other inventors or manufacturers may claim that, while their products contain potentially comedogenic or irritating ingredients, the concentrations of these comedogenic or irritating chemicals are too small to cause any clinical difficulty when applied to a patient's skin. Fulton, however, makes the key point that "[t]he major offenders, such as isopropyl myristate, acetylated lanolin alcohol and lauric acid derivatives such as laureth-4, should be used with caution in skin care products. We are not convinced of the statement that lower concentrations of these compounds can be safely used with no comedogenic consequences. Human skin studies have been used to give that statement credence, but the back skin of human volunteers is relatively insensitive. However, when the rabbit ear assay is positive but the human back skin results are negative after only 8 weeks' exposure, the results from the rabbit ear assay should not be dismissed. The reaction may take longer or the back skin may not be the ideal testing surface." See Fulton, page 332 (citations omitted).

Why, then, have skin care compositions such as those of the present invention never before been formulated? One consideration is the ready availability of inexpensive chemicals, such as petrolatum or mineral oil. Another factor is the tendency to repeat endlessly minor variations of older formulas in existence for many years. Additionally, larger manufacturers may simply be able to afford to ignore the 1% to 2% of patients who develop acne or contact dermatitis, reasoning that a refund may be expeditious from a business sense. Finally, the restriction of an ingredient formulary to items rated 0 or 1 for comedogenicity and irritancy greatly reduces the chemicals available for inclusion in such a product line.

In the antipruritic compositions of the invention, the carrier is preferably a cream. A suitable cream will comprise distilled water, a wax, an emulsifier and a preservative. The cream may also contain an opacifier, an emollient, and/or a suncreen. Preferably, the cream contains about 10% to 50% distilled water, about 5% to 25% wax, about 1% to 15% emulsifier, about 0.01–0.25% preservative, about 1% to 10% opacifier, and about 1% to 10% emollient. All percentages are w/w based on the total weight of the composition.

Suitable waxes include ceresin wax, candelilla wax, carnuba wax and emulsifying wax NF. Presently preferred is emulsifying wax NF in a range 5 to 25%.

Suitable emulsifiers include diisopropyl dimerate, octyldodecyl stearate, octyldodecyl stearoyl stearate, sorbitan sesquioleate, glyceryl stearate NSE, behenyl triglyceride, pentaerythritol tetra capra/caprylate, sucrose stearate, PEG 100 stearate, steareth-100, PPG 30 cetyl ester, PPG 50 cetyl ester, polypentaerythrital tetralaurate, PEG 120 methyl glucose dioleate, C12–15 alkyl (alkyl containing 12–15 carbon atoms) benzoate, and amoniomethylpropinate. Presently preferred are sorbitan sesquioleate in a range of 1 to 5%, PEG 120 methyl glucose dioleate in a range of 1 to 4%, and C12–15 alkyl benzoate in a range of 1 to 5%.

Suitable preservatives include methyl paraben, propyl paraben, butyl paraben, phenoxyethyl paraben, phenoxyethyl alcohol, precipitated sulfur, and sorbic acid and other sorbates. Presently preferred are methyl paraben in a range of 0.05 to 0.15% and propyl paraben in a range of 0.03 to 0.1%.

Suitable opacifiers include behenic acid and tribehenin. Presently preferred is behenic acid in a range of 2 to 7%.

Suitable emollients include cetyl palmitate, diisopropyl adipate, polysorbate 20, polysorbate 80 (Tween 80), glycereth-26, sodium hyaluronate, chondroitin sulfate and allantoin. Presently preferred are polysorbate 20 in a range of 1 to 5%, and polysorbate 80 in a range of 1 to 3%.

Suitable sunscreens include octyl methoxycinnamate and other cinnamates, octyl salicylate, oxygenzone, octyl dimethyl PABA and other PABA esters in ranges of approximately 5% to approximately 15%. The increasing worldwide prevalence of skin cancer (including basal cell carcinoma, squamous cell carcinoma and malignant melanoma) has led many formulators to include suncreens in skin care products applied to exposed areas. The compositions of the present invention employ ingredients providing adequate sun protection while avoiding comedogenicity and irritancy.

The antipruritic compositions of the invention comprise menthol, camphor and phenol as active ingredients. Preferably, the compositions contain camphor in a range of about 0.5% to 1.5%, menthol in a range of about 0.5% to 1.5%, and phenol in a range of about 0.5% to 1.0%.

The antipruritic compositions of the invention preferably comprise lidocaine and pramoxine as additional active ingredients. Preferably, the compositions contain about 1% to 10% lidocaine and about 1% to 2.5% pramoxine.

Finally, the antipruritic compositions may comprise hydrocortisone acetate as a further active ingredient. Preferably the compositions contain about 1% to 5% hydrocortisone acetate.

Pruritus, when present, can be a maddening symptom. This problem can have many etiologies. Contact dermatitis, xerosis, irritant dermatitis, drug reactions, stress or tension, varicella, sun burn, dermatitis herpetiformis, scabies, and internal diseases, such as malignancy or renal failure, can all cause severe, acute, sub-acute, or chronic pruritus.

A number of active ingredients have been approved by the U.S. Food & Drug Administration (FDA) for inclusion in over-the-counter products at, or under, the allowable concentrations. Menthol, camphor, or phenol can all relieve pruritus, but have not been used simultaneously, even though their combination produces a eutectic mixture. Pramoxine is anti-pruritic but, prior to the present invention, had only been combined with hydrocortisone. Lidocaine or other related anesthetics are generally used internally or as sole ingredients of topical jellies or ointments.

A market survey of current anti-itch products reveals the following characteristic existing combinations: Aveeno Anti-itch Cream with 3% Calamine and 1% Pramoxine; Benedryl with 1% Diphenydramine; Benedryl Relief Stick with 2% Benedryl; Blistex anti-itch Medicated Lotion with 1% Pramoxine and 1% Dimethicone; Caladryl Pain and Itch Relieving Medication with 8% Calamine and 1% Pramoxine; Caladryl Clear Lotion with 1% Promoxine; Cortaid Cream with Aloe with 0.25% Hydrocortisone; Gold Bond Medicated Anti-itch Cream with Lidocaine and Menthol; Lanacaine Anti-itch Cream with 6% Benzocaine; and Sarna Anti-itch cream with Camphor and Menthol. Additional products such as Vicks Vaporub also contain Camphor and Menthol.

The employment of external topical analgesics is discussed in the Federal Register, Part 2, dated Dec. 4, 1979, Volume 44, No. 234, pps 69765–69791, 69864, 69865 and 69866. Use of topical analgesics is further discussed in the Federal Register dated Tuesday, Feb. 8, 1983, Volume 48, No. 27, pps 5867, 5868 and 5869. A further description of anti-itching products can be found in the American Pharmaceutical Association's "Handbook for Prescription Drugs", published by the National Professional Society of Pharmacists, 215 Constitution Avenue Northwest, Washington, DC 20037, 8th Edition 1986, Chapter 31.

The compositions of the invention can be used to treat pruritis by applying an effective amount of the composition to the skin. Such effective amounts are known in the art or can be determined empirically as is known in the art. In particular, the compositions of the invention can be used to treat contact dermatitis, irritant dermatitis, contact or generalized uticaria, seborrheic dermatitis, post operative laser pruritus, sunburn, atopic dermatitis, drug reactions, rashes, other pruritic dermatosis, and itching due to dry skin or aging.

Although antipruritc compositions comprising carrier ingredients rated 0 or 1 with respect to comedogenicity and irritancy will generally be noncomedogenic, nonacnegenic and hypoallergenic, the complete composition should be tested to ensure that this is, in fact, the case. This testing can be performed as described in Fulton, *J. Soc. Cosmet. Chem.*, 40, 321–333 (November/December 1989) (see above). Alternatively, testing on humans may be employed (see, e.g., Example 2 below).

EXAMPLES

Example 1

The following example describes the preparation of antipruritic creams comprising 5–25% emulsifying wax NF, 2–7% behenic acid, 1–4% PEG 120 methyl glucose dioleate, 1–5% polysorbate 20, 1–3% polysorbate 80, 1–5% sorbitan sesquioleate, 0.05–0.15% methyl paraben, 0.03–0.10% propyl paraben, 0.5–1.5% menthol, 0.5–1.5% camphor, 0.5–1.0% phenol, 1–10% lidocaine, 1–2.5% pramoxine, 10–50% distilled water, and 1–5% C12–15 alkyl benzoate. These creams can be used to treat pruritis by applying a thin layer to the skin 2–3 times daily for 1–10 or more days.

To prepare the creams, the emulsifying wax, behenic acid, and PEG 120 methylglucose dioleate were melted at approximately 65° C. To this mixture were added the polysorbate 20, polysorbate 80, sorbitan sesquioleate and the parabens. Next, the menthol, camphor and phenol were combined into a eutectic mixture and added to the above mixture. Next, the distilled water was warmed to 60° C., and the lidocaine and pramoxine were dissolved in the warmed water. While still warm, the water phase was beaten and, then, added to the oil phase. Next, the C12–15 alkyl benzoate, in paste form, was levigated into the emulsion as cooling occurred. This product was placed in suitable jars or bottles.

Example 2

The creams prepared in Example 1 were tested on human volunteers as follows to determine their safety and efficacy in the control of cutaneous pruritus.

Patients were chosen for inclusion in the trial if they satisfied the following criteria:
1. Pruritus score of 2, 3 or 4 (criteria listed below)
2. Willingness to sign Informed Consent
3. Willingness to participate in 7 Day Clinical Trial
4. Willingness to apply medication as directed and return for two more study visits
5. Sufficient itching area size to allow performance of paired comparison study.

Patients were excluded from the study for the following reasons:
1. Nursing or pregnant females
2. Use of other medications or topical steroids that in the opinion of the clinical investigator would invalidate the objectivity of the study
3. An inability to follow the study protocol
4. Inability to return for all study visits.

The patients were given one jar of medication marked with a red dot which they were instructed to apply three times daily to the right side of the itching area. This was a negative control containing the cream base but without menthol, camphor, phenol, lidocaine, pramoxine or hydrocortisone. They were also given another jar or bottle marked with a green dot which they were instructed to apply to the left side of the itching area. This jar contained the full antipruritic cream composition listed above.

The patients were rated on days 0, 1 and 7 using the following criteria:

| Objective Criteria: Rate 0 to 4 (Physician rating) | Subjective Evaluation: Rate 0 to 4 (Patient Rating) |
|---|---|
| 1  Erythema/Dermatitis | 0 = None |
| 2  Vesiculation | 1 = Slight |
| 3  Acne | 2 = Moderate |
| A  Papules | 3 = Bothersome |
| B  Pustules | 4 = Severe |
| C  Cysts | 1  Itching |
| D  Comedones | 2  Burning |
| E  Milia | 3  Redness/Rash |
|  | 4  Stickiness, oiliness or greasiness |
|  | 5  Spreadability - rubs in well |
|  | 6  Dryness and flaking |
|  | 7  Improvement in my skin aging signs |
|  | 8  Improvement in my skin pigmentation |

All of the patients reported improvement in their pruritis using the creams of Example 1 (from a rating of 2–4 to a rating of 0 to 2 with an average of approx. 1). Also, all of the creams were found to be noncomedogenic, nonacnegenic, nonirritating, and hypoallergenic (ratings of 0 or 1).

The above discussion of the invention is directed primarily to preferred embodiments and practices thereof. It will be readily apparent to those skilled in the art that further changes and modifications in the actual implementation of the concepts described herein can readily be made without departing from the spirit and scope of the invention as defined by the following claims.

I claim:

1. A hypoallergenic, noncomedogenic, nonacnegenic, antipruritic composition which is oil-free, lanolin-free, fragrance-free, and free of Imidazolidinyl urea, quaternium-15, germall, the composition comprising about 0.5% to 1.5% menthol, about 0.5% to 1.5% camphor, about 0.5% to 1.0% phenol, about 1% to 10% lidocaine, about 1% to 2.5% pramoxine, about 10% to 50% distilled water, about 5% to 25% emulsifying wax NF, about 2% to 7% behenric acid, about 1% to 4% PEG 120 methylglucose dioleate, about 1% to 5% polysorbate 20, about 1% to 3% polysorbate 80, about 1% to 5% sorbitan sesquioleate, about 0.5% to 0.15% methyl paraben, about 0.3% to 0.10% propylparaben, about 1% to 5% C12–15 alkyl benzoate in a carrier containing only those ingredients rated 0 or 1 with respect to comedogenicity and irritancy.

2. The composition of claim 1 wherein the carrier is a cream.

3. The composition of claim 1 further comprising hydrocortisone acetate.

4. The composition of claim 3 comprising about 1% to 5% hydrocortisone acetate.

5. The composition of claim 3 wherein the carrier is a cream.

6. A method of making the composition of claim 1 comprising:

combining menthol, camphor, and phenol to form a eutectic mixture and then adding this mixture to ingredients: emulsifying wax NF, behenic acid, PEG 120 methylglucose dioleate, polysorbate 20, polysorbate 80 sorbitan sesquioleate, methyl paraben, propyl paraben, and C12–15 alkyl benzoate so as to form an oil phase;

dissolving lidocaine and pramoxine in water; and adding the aqueous solution of lidocaine and pramoxine to the oil phase containing the menthol, camphor and phenol to form an emulsion.

7. A method of treating pruritic skin comprising the application of an effective amount of composition of any one of claims 1 or 3 to the skin.

* * * * *